United States Patent [19]

Mönch

[11] Patent Number: 5,372,265
[45] Date of Patent: Dec. 13, 1994

[54] MOBILE SURGICAL APPARATUS TABLE

[75] Inventor: Harry Mönch, Knittlingen, Germany

[73] Assignee: Riwoplan medizin-technische Einrichtungsgesellschaft mbH, Knittlingen, Germany

[21] Appl. No.: 67,448

[22] Filed: May 25, 1993

[30] Foreign Application Priority Data

May 27, 1992 [DE] Germany .............. 4217501

[51] Int. Cl.⁵ .............................................. A47F 5/00
[52] U.S. Cl. .................................. 211/187; 211/133
[58] Field of Search .............. 211/187, 133, 207; 108/107

[56] References Cited

U.S. PATENT DOCUMENTS

| | | | |
|---|---|---|---|
| 869,491 | 10/1907 | Hurteau | 108/107 |
| 3,999,775 | 12/1976 | Brongo | 211/187 X |
| 4,568,050 | 2/1986 | Radoy et al. | 211/187 X |
| 5,088,607 | 2/1992 | Rusafir et al. | 211/187 X |
| 5,094,350 | 3/1992 | Smock | 211/187 X |

FOREIGN PATENT DOCUMENTS 0381240 8/1990 European Pat. Off. .
3402885 8/1984 Germany .
3918162 10/1990 Germany .

*Primary Examiner*—Alvin C. Chin-Shue
*Assistant Examiner*—Sarah L. Purol
*Attorney, Agent, or Firm*—Panitch Schwarze Jacobs & Nadel

[57] ABSTRACT

An apparatus table is described which has two lateral stands provided with attachment means and arranged at a fixed distance with respect to one another and at least one receiving device for instruments, apparatus and the like, provided between the stands, the receiving device being screwed to the two stands. To achieve a simply constructed receiving device which can be manufactured inexpensively, the receiving device has structural components assembled in the form of movable parts and comprising two opposing edge strips screwed in each case to the associated stand and extending transversely thereto with plug-in receivers and a working shelf provided with plug-in projections which project into the plug-in receivers. Each stand has two vertical, projecting bearing rails for the particular edge strip at a distance from one another on its side facing the edge strip attached to the stand. The stands have the attachment means for the receiving devices between the bearing rails.

4 Claims, 1 Drawing Sheet

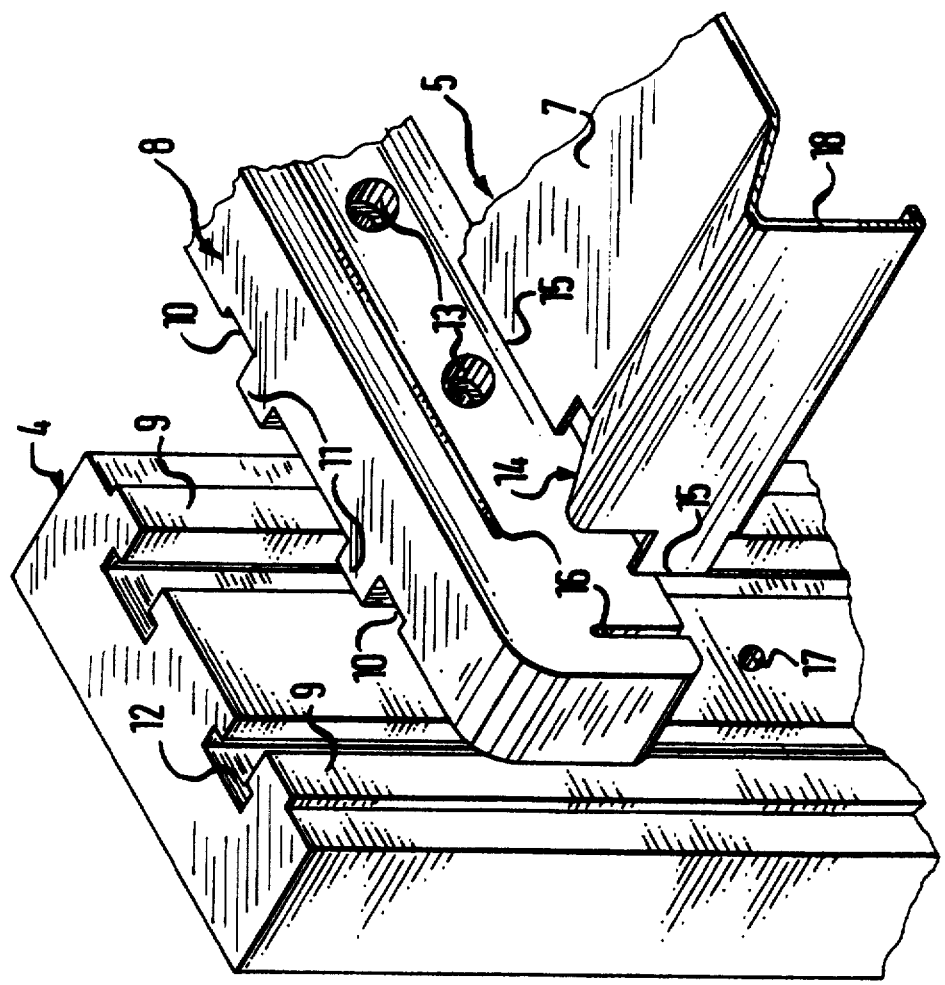
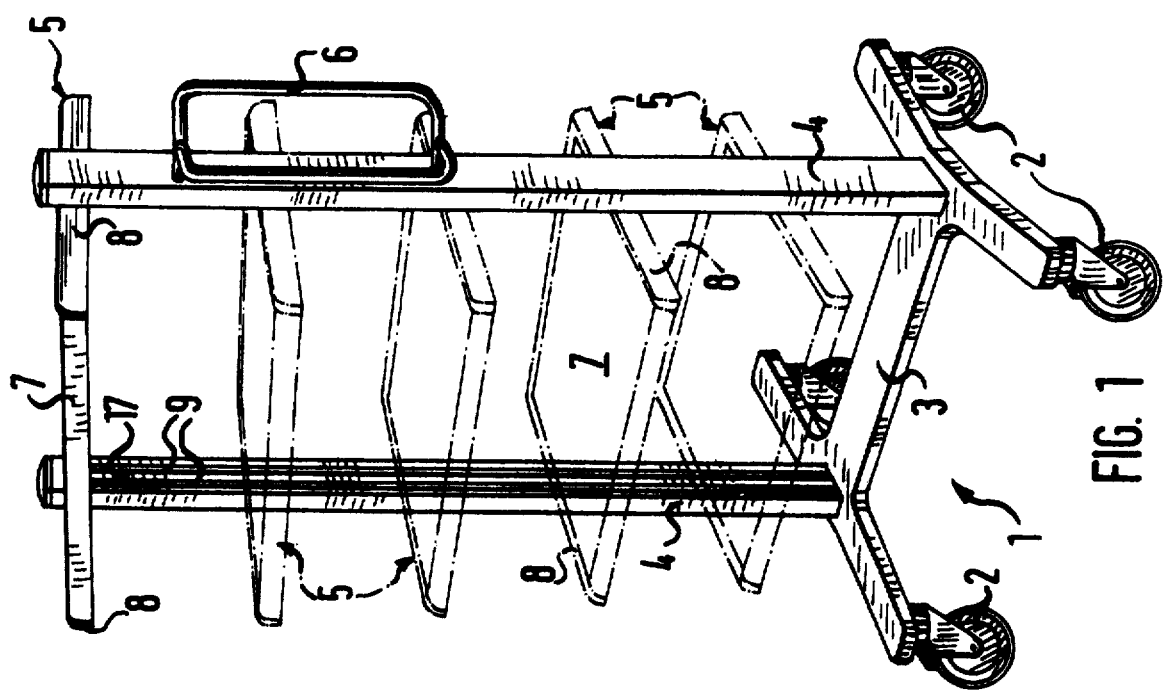

MOBILE SURGICAL APPARATUS TABLE

BACKGROUND OF THE INVENTION a) Field of the Invention

The invention relates to a mobile surgical apparatus table having two lateral stands provided with attachment means and arranged at a fixed distance with respect to one another and having at least one shelf-like receiving device for instruments, apparatus and the like, provided between the stands, the device being releasably connected to the two stands at their attachment means by means of screws.

b) Description of the Prior Art

An apparatus table of this type is described in German Patentschrift 3 918 162. That document discloses a support frame comprising two vertical stands and having several receiving devices, for example a working shelf, the shelf being screwed to the two stands. The or each working shelf comprises an inner stiffening shelf with crossarms extending in the longitudinal direction arranged on its lower side, as well as an upper and a lower plastic moulding completely surrounding the stiffening shelf and the crossarms. The upper plastic moulding thus overlaps in each case the end-face sides of the stiffening shelf. During manufacture, the two plastic mouldings are then welded to one another at their common edges, so that the inner stiffening shelf and the crossarms are embedded positively between the two plastic mouldings. The working shelf constructed in this manner is attached to the two stands by means of screws which are passed through holes on the transverse edges of the working shelf. Although working shelves of this type have proved worthwhile, the effort in terms of material and cost is relatively high for their manufacture.

The object of the invention is to improve a mobile surgical apparatus table of the type indicated, to the effect that its receiving device can be manufactured with simpler construction and at more favourable cost while maintaining its rigidity and secure attachment to the stands.

SUMMARY OF THE INVENTION

This object is achieved by a mobile surgical apparatus table having two lateral stands provided with attachment means and arranged at a fixed distance with respect to one another and having at least one shelf-like receiving device for instruments, apparatus and the like, provided between the stands, the device being releasably connected to the two stands at their attachment means by means of screws, wherein the receiving device has structural components assembled in the form of movable parts comprising two opposing edge strips screwed in each case to the associated stand and extending transversely thereto with plug-in receivers and a working shelf provided with plug-in projections which project into the plug-in receivers, each stand having two upright, projecting bearing rails for the edge strip at a distance from one another on its side facing the edge strip attached to the stand, and the attachment means of the stands for the edge strips being provided between the bearing rails.

The manufacturing effort for the apparatus table in terms of material and time as a whole is considerably reduced as a result of this solution, since the shelf-like receiving device, which may be supplemented by added drawers and other storage, has a simpler construction. In its simplest form, the receiving device consists of a storage shelf construction, that is without drawers or other attachments connected thereto, this shelf construction having considerably fewer components compared to the work receiving shelves according to the patent specification mentioned in the introduction. The storage shelf construction in practice consists of only three parts which are movably assembled. The shelf construction is held together solidly due to the screwing of the assembled parts to the two stands having a fixed distance from one another. A further advantage is that greater manufacturing tolerances may be selected without the fitting accuracy of all assembled parts suffering as a result. The design of the stands with bearing rails can be effected in a simple manner, and these rails cause slight distortion of these edge strips when screwing the edge strips of the receiving device to the stands, as a result of which they are pressed against the shelf part of the receiving device, so that slots or gaps between the shelf part and the edge strips of the receiving device leading to injury or retaining dirt are avoided.

In an advantageous further embodiment of the apparatus table of the invention, each stand is provided with at least one vertical slotted link, for example in T shape, in which a conventional sliding block is provided. The receiving device is screwed to the sliding block in this case. The height of the receiving device can be adjusted continuously in this manner.

Furthermore, each edge strip of the receiving device may have at least one guide rail which is guided between the bearing rails of the associated stand while resting against it or engages in the slotted link of the associated stand. This ensures that the receiving device is always aligned vertically to the two stands in the horizontal direction.

It is preferred that each working shelf consisting of plastic or metal has an angular wall edge at its longitudinal edges, whereas the edges of each working shelf facing the edge strips are without walls, and that the corner regions of each working shelf are provided with a material recess to form vertical and horizontal plug-in projections.

BRIEF DESCRIPTION OF THE DRAWINGS

The foregoing summary of the invention, as well as the following detailed description of the preferred embodiments, will be better understood when read in conjunction with the appended drawings. For the purposes of illustrating the invention, there are shown in the drawings embodiments which are presently preferred, it being understood, however, that the invention is not limited to the specific arrangements and instrumentalities disclosed. In the drawings:

FIG. 1 shows the exemplary embodiment in perspective view; and

FIG. 2 shows a partial perspective view of an exploded representation of a region of the receiving device and of a section of a stand of the apparatus table.

DESCRIPTION OF THE PREFERRED EMBODIMENTS

The mobile surgical apparatus table generally designated 1 in FIG. 1 comprises a base 3 mounted on steerable rollers 2, to which base 3 two stands 4 are attached at a fixed distance with respect to one another and which support several receiving devices 5 arranged between them. At least one of the stands 4 is provided with a handle 6 in order that the table 1 can be moved easily. As shown, the receiving devices 5 have a simple shelf construction, on which surgical instruments, apparatus and the like, are stored. Shelf constructions of this type may be extended by means of drawers added on underneath or other support devices, but this is not shown.

Each receiving device 5 comprises structural components comprising at least three parts which are assembled with one another as movable parts, namely a working shelf 7 consisting of plastic or metal and two plastic edge strips 8 extending transversely, arranged at the two narrow sides of the working shelf 7.

Each stand 4 has on its side facing the edge strip of each receiving device 5, two vertical, projecting bearing rails 9 for the opposite edge strip 8 at a distance from one another. The bearing surfaces 10, designed as fiat grooves in the case shown, of the edge strip 8 come to rest against these bearing rails 9. Each edge strip 8 has at least one guide rail 11. In the case shown, there are two guide rails 11 which each come to rest against the inner side of the bearing rail 9. This ensures that the receiving device 5 is always aligned vertically to the stand 4 in the horizontal direction.

Each stand 4 is also provided with attachment means for the or each receiving device. These attachment means preferably comprise at least one T-shaped slotted link 12, in which the conventional sliding blocks with threaded bores are provided. The relevant edge strips 8 have corresponding access holes 13, through which screws, not shown, extend and engage in the sliding blocks. The edge strips 8 are pressed against the bearing rails 9 by tightening the screws and thus frictionally attach to the stands 4.

The slotted links 12 with the corresponding sliding blocks make it possible to continuously adjust the work receiving devices 5 at the particular height required. Alternatively to this, if continuous adjustment is not required, a procedure may also be carried out so that simple threaded bores, in which the screws extending through the access holes 13 in the edge strips 8 then engage, are provided in the stands 4 instead of the slotted links 12.

If slotted links 12 are selected, an alternative procedure may be carried out so that the guide rails 11 at the same time also project slightly into the slotted links. Guiding the edge strips 8 at the stands 4 is also easy and secure, or the receiving devices 5 may be easily adjusted as a result.

The receiving device 5 assembled from movable parts comprises a very simply shaped working shelf 7. This working shelf has an angular, for example vertical, wall edge 18 at its two longitudinal edges and hence gives the entire shelf a rigid form. The two narrow sides of the shelf 7 are without walls. Furthermore, the corner regions of the shelf 7 are each provided with a material recess 14, so that the shelf 7 has rib-like projecting plug-in projections 15 at its narrow sides, the lateral plug-in projections 15 extending vertically. To correspond to these plug-in projections each edge strip 8 has plug-in receivers 16, into which the plug-in projections 15 are inserted or engage.

It can be seen from the above comments in conjunction with FIG. 2 in particular, that the receiving device 5 has a very simple construction and hence may be manufactured inexpensively. Since the access holes 13 of each edge strip are at a shorter distance from one another than the guide rails 9 on the stands 4, and after resting the surfaces 10 against the rails 9, the edge strip 8 is also at a shorter distance from the stand 4 in the region between the two guide rails 11, when tightening the screws penetrating the holes 13, the result is that the end regions of the edge strips are pressed against the corner regions of the working shelf 7, because the edge strips bend slightly concavely in the direction of the shelf 7. Any gaps present, which could lead to injury and/or soiling, between the corner regions of the shelf 7 and the particular edge strip 8 are thus adjusted, particularly if the recesses 14 are manufactured with a relatively large tolerance.

In order to ensure secure attachment of the receiving devices 5 to the stands 4, they are connected to one another by means of a strut (not shown) at their upper end region. The stands have additional threaded bores 17 for this, by means of which the corresponding strut is screwed.

The present invention may be embodied in other specific forms without departing from the spirit or essential attributes thereof and, accordingly, reference should be made to the appended claims rather than to the foregoing specification as indicating the scope of the invention.

I claim:

1. Mobile surgical apparatus table having two lateral stands provided with attachment means and arranged at a fixed distance with respect to one another and having at least one shelf-like receiving device for instruments, apparatus and the like, provided between the stands, the device being releasably connected to the two stands at their attachment means by means of screws, wherein the receiving device has structural components assembled in the form of movable parts comprising two opposing edge strips screwed in each case to the associated stand and extending transversely thereto with plug-in receivers and a working shelf provided with plug-in projections which project into the plug-in receivers, each stand having two upright, projecting bearing rails for the edge strip at a distance from one another on its side facing the edge strip attached to the strand, and the attachment means of the stands for the edge strips being provided between the bearing rails.

2. Apparatus table according to claim 1, wherein the attachment means of the stands comprise in each case at least one vertical slotted link with sliding blocks.

3. Apparatus table according to claim 1, wherein each edge strip of the structural components has at least one guide rail which is guided between the bearing rails of the associated stand while resting against it or engages in the slotted link of the associated stand.

4. Apparatus table according to claim 1, wherein each working shelf consisting of plastic or metal has an angular wall edge at its longitudinal edges, whereas the edges of each working shelf facing the edge strips are designed to be without walls, and wherein the corner regions of each working shelf are provided with a material recess to form vertical and horizontal plug-in projections.

* * * * *